(12) United States Patent
Propp (10) Patent No.: US 8,486,004 B1
(45) Date of Patent: Jul. 16, 2013

(54) DRESSING HAVING INTEGRAL ANTIMICROBIAL

(75) Inventor: Donald J. Propp, Dewitt, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 131 days.

(21) Appl. No.: 12/821,420

(22) Filed: Jun. 23, 2010

Related U.S. Application Data (60) Provisional application No. 61/222,511, filed on Jul. 2, 2009.

(51) Int. Cl.
 *A61M 31/00* (2006.01)
 *A61M 5/32* (2006.01)

(52) U.S. Cl.
 USPC ............................. 604/48; 604/178; 604/180

(58) Field of Classification Search
 USPC ............... 602/41–58; 604/180; 128/877–879, 128/888; 424/443, 447, 448, 449
 See application file for complete search history.

(56) References Cited

U.S. PATENT DOCUMENTS

| | | | | |
|---|---|---|---|---|
| 4,615,334 A | * | 10/1986 | Jaeger | 600/195 |
| 5,295,950 A | * | 3/1994 | Godley | 602/53 |
| 5,686,096 A | * | 11/1997 | Khan et al. | 424/443 |
| 5,885,254 A | * | 3/1999 | Matyas | 604/180 |
| 6,998,511 B2 | * | 2/2006 | Worthley | 602/57 |
| 2005/0027258 A1 | * | 2/2005 | Bierman et al. | 604/174 |
| 2005/0249791 A1 | * | 11/2005 | Hobbs et al. | 424/443 |
| 2009/0192470 A1 | * | 7/2009 | Propp | 604/180 |
| 2011/0282291 A1 | * | 11/2011 | Ciccone | 604/178 |

* cited by examiner

*Primary Examiner* — Patricia Bianco
*Assistant Examiner* — Ophelia A Hawthorne
(74) *Attorney, Agent, or Firm* — Rader, Fishman & Grauer, PLLC (57) ABSTRACT

A dressing having integral antimicrobial includes a transparent film layer having a top side, an opposite bottom side, and an insertion site viewing portion. The dressing also includes an antimicrobial member having a top side and an opposite bottom side. The antimicrobial member top side is adhered to the film layer bottom side in the insertion site viewing portion. The antimicrobial member includes at least one pair of elongated, spacedly disposed portions defining a slot therebetween. A zone of inhibition defined by the antimicrobial member covers an entire area of the slot between the member portions.

26 Claims, 11 Drawing Sheets

DRESSING HAVING INTEGRAL ANTIMICROBIAL

CROSS REFERENCE TO RELATED APPLICATION

This application claims the priority of U.S. Provisional Application No. 61/222,511 filed Jul. 2, 2009.

TECHNICAL FIELD

This invention relates to medical dressings, and more particularly to self-adherent catheter care dressings for the viewing and protection of PIA, PIV, PICC, CVC, IJ, subclavian, epidural, femoral, implant port catheters, and similar catheters about a catheter insertion site.

BACKGROUND OF THE INVENTION

It is known in the art relating to medical dressings for the protection and securement of catheters to apply a dressing to a patient's skin to cover a catheter insertion site at which the catheter punctures a patient's skin. It is also a conventional practice for medical clinicians (i.e., doctors, nurses, and other medical personnel) to separately apply an antimicrobial material (patch, liquid, ointment, etc.) at, around, or over the insertion site to protect the insertion site against the risk of infection.

However, conventional antimicrobial materials are cumbersome to use with catheter insertion site dressings because the antimicrobial material is separate from the dressing and must be applied prior to the positioning of the dressing over the insertion site. Further, some antimicrobial materials do not adequately protect all the surface area of a patient's skin around the catheter, due to the catheter hub holding the antimicrobial dressing/material up and away from the patient's skin, resulting in no contact "tenting" areas. Such an incomplete zone of inhibition decreases the effectiveness of the antimicrobial material. Hence, conventional antimicrobial materials do not consistently, reliably, and sufficiently protect catheter insertion sites against infection. Further, additional labor and material costs of two dressings/devices are needed. Therefore, a single, unified, integrated one-piece antimicrobial dressing has been a need, long-felt but heretofore unmet.

SUMMARY OF THE INVENTION

The present invention provides a dressing having an integral antimicrobial element that is capable of integration into the simplest dressing, such as a single layer TSM (e.g., transparent semipermeable polyurethane film membrane dressing), up to and through multi-layer high functionality dressings with integrated anchoring. The integrated dressing includes an integral antimicrobial material (CHG, silver, or similar) having up to a 7 day dwell and controlled release, allowing for easy alignment of the integral antimicrobial portion with the catheter and insertion site at the same time that the dressing is applied to a patient's skin. The dressing also provides a zone of inhibition up to some distance away from the edges of the antimicrobial portion that completely surrounds and reaches the catheter insertion site and completely covers the patient's skin in the region of the antimicrobial material.

More particularly, a dressing having integral antimicrobial in accordance with the present invention may include a transparent film layer having a top side, an opposite bottom side, and an insertion site viewing portion. An antimicrobial member having a top side and an opposite bottom side is adhered to the film layer. Specifically, the antimicrobial member top side may be adhered to the film layer bottom side in the insertion site viewing portion. The antimicrobial member includes at least one pair of elongated, spacedly disposed portions defining an open-ended slot or U-channel therebetween. A zone of inhibition defined by the antimicrobial member covers an entire area of the slot between the member portions.

The film layer bottom side may include an adhesive thereon. The film layer bottom side may include an adhesive portion and an adhesive-free portion. The adhesive-free portion may be disposed in the slot between the antimicrobial member portions.

The antimicrobial member bottom side may include an adhesive thereon. The antimicrobial member bottom side may also include an adhesive free portion adjacent the slot. Alternatively, the antimicrobial member bottom side may have no adhesive thereon. The slot may have a width approximately in the range of 0.05 inches to 0.4 inches. The antimicrobial member may include at least one of an antimicrobial agent, an antifungal agent, an antiseptic agent, an antibacteriocidal agent, and an antiviral agent. The adhesive may also include at least one of an antimicrobial agent, an antifungal agent, an antiseptic agent, an antibacteriocidal agent, and an antiviral agent. The antimicrobial member may be made of a carrier material such as a foam material or similar impregnated with an antimicrobial agent and including a slow release binder.

The antimicrobial member portions may be generally parallel and spacedly disposed in proximity to each other. The antimicrobial member portions may be disconnected. Alternatively, the antimicrobial member may be bifurcated such that the portions define prongs of the bifurcated antimicrobial member. Optionally, the antimicrobial member may include at least one tie connecting the portions. The tie may have a height that is less than a height of the portions. Each portion may include a curved sidewall adjacent the slot. Each portion may also include a blade extending from the curved sidewall towards the other of the portions. Alternatively, each antimicrobial member portion may include a sloped sidewall such that the slot is tapered towards the antimicrobial member bottom side. Alternatively, each portion may include a sidewall adjacent the slot that has a scalloped surface facing the slot. Optionally, the antimicrobial member may include a carrier layer comprising a foam material or similar and an adjacent fibrous layer comprising a cotton material or similar.

The dressing may further include a fabric layer having a top side, an opposite bottom side, and an opening therein. The fabric layer may be adhered to one of the film layer top side and the film layer bottom side. The opening may define the insertion site viewing portion.

The dressing may also include an absorbent pad adhered to the film layer bottom side. The absorbent pad may be generally disposed in or adjacent to the insertion site viewing portion. The absorbent pad may be generally disposed outside of the antimicrobial member. The dressing may also include an absorbent pad link member that connects the absorbent pad to the antimicrobial member.

The dressing may also include an anchor member including a reinforcing structure. The anchor member may be adhered to one of the fabric layer top side and the fabric layer bottom side. The anchor member may be disposed between the fabric layer and the film layer. The anchor member also may be disposed outside of the insertion site viewing portion.

These and other features and advantages of the invention will be more fully understood from the following detailed description of the invention taken together with the accompanying drawings.

DETAILED DESCRIPTION OF THE INVENTION

Referring now to the drawings in detail, numeral 110 generally indicates a dressing having an integral antimicrobial. The dressing provides a zone of inhibition directly under and up to some distance away from any of the edges of the antimicrobial portion that completely surrounds and reaches the catheter insertion site and completely covers the patient's skin in the region of the antimicrobial material.

Figure 1:
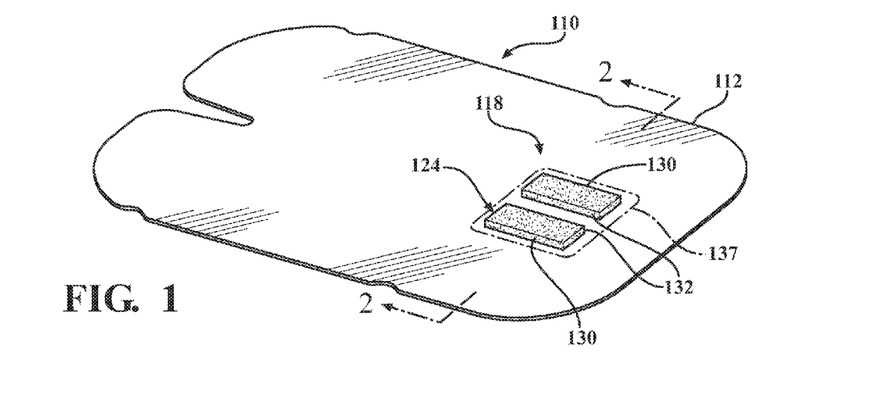
FIG. 1 is a perspective view of a dressing having integral antimicrobial in accordance with the present invention.
Figure 2:
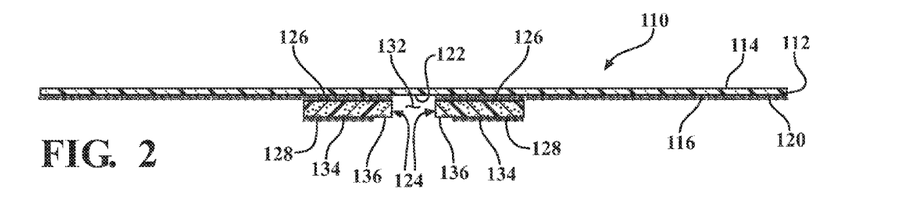
FIG. 2 is a cross-sectional view taken along the line 2-2 in FIG. 1.

Turning to FIGS. 1 and 2, an integrated antimicrobial dressing 110 in accordance with the invention includes a first layer 112 which may be a transparent semipermeable film layer such as a polyurethane film or similar. The first layer 112 alternatively may be a fabric layer such as a woven or nonwoven fabric. The transparent film layer 112 has a top side 114, an opposite bottom side 116, and an insertion site viewing portion 118 within the boundaries of the film layer. The film layer bottom side 116 may include an adhesive thereon. For example, the film layer bottom side 116 may include an adhesive portion 120 having an adhesive thereon that is used to attach other members to the bottom side 116. Generally, the adhesive portion 120 extends across the entire film layer bottom side 116. Optionally, however, the film layer bottom side 116 may also optionally include an adhesive-free portion 122 that is generally free of adhesive. The adhesive-free portion 122 may improve the see-through visibility of a catheter insertion site (on one side) through the film layer 112.

An antimicrobial member 124 having a top side 126 and an opposite bottom side 128 is adhered to the film layer 112. Specifically, the antimicrobial member top side 126 is adhered to the film layer bottom side 116 in the insertion site viewing portion 118. The antimicrobial member 124 includes at least one pair of elongated, spacedly disposed portions 130 defining an insertion site/catheter lumen accepting slot 132 therebetween. The optional adhesive-free portion 122 of the film layer bottom side 116 may be generally disposed in the slot 132 between the antimicrobial member portions 130. The antimicrobial member bottom side 128 may include an adhesive thereon, and the antimicrobial member bottom side may include both an adhesive portion 134 and an adhesive free portion 136 adjacent the slot. Alternatively, the antimicrobial member bottom side may have no adhesive thereon. The optional adhesive portion 134 reduces shifting of the antimicrobial member 124 on irregularly shaped patient body features about the insertion site. The adhesive on the adhesive portion 134 may be continuous, or it may be interrupted, discontinuous, patterned, dotted, island shaped, or may have round or other shaped adhesive voids to facilitate agent leach out from the antimicrobial member to the skin, such that the adhesive is preferably breathable (i.e., permeable), and may not interfere with, impede on, or retard the slow release of antimicrobial agent (see below) from the antimicrobial member 124 through the adhesive layer. The adhesive free portion 136 facilitates placement of the antimicrobial member 124 over an insertion site and/or catheter lumen. The antimicrobial member 124 may be made of a foam layer such as a hydrophilic polyurethane foam or similar that has absorbency. Alternatively, the antimicrobial member 124 may be partially or entirely made from viscose, gel(s), hydrogel(s), hydrocolloid(s), fabric, cellulose, rayon, or similar as a carrier material for the antimicrobial agent(s). The material of the antimicrobial member 124 is not particularly limited so long as it is capable of carrying (e.g., binding) and releasing (e.g., slow-releasing) an antimicrobial and/or antifungal agent.

The antimicrobial member 124 may include an active antimicrobial agent and/or an antifungal agent and/or an antiseptic agent including but not limited to chlorhexidine gluconate (CHG), silver compounds such as silver alginate, silver ionic colloids or similar, Microban® triclosan, minocycline-rifamdin, silver-platinum-carbon, chlorhexadine-silver-sulfadiazine, or others. For example, the antimicrobial member 124 may be a foam material (e.g., polyurethane foam or similar) impregnated with CHG including slow release binders and slow release properties. Alternatively, the antimicrobial member 124 may be a gel material that includes CHG, although the antimicrobial member may be made of any material capable of carrying and releasing an active antimicrobial agent. When the dressing is applied on a patient, the antimicrobial member delivers the active agent for a period of generally from time zero (time of application on patient) to up to at least seven to ten days. Also, the antimicrobial member (foam, gel, pad, etc.) may include binders or mediator compounds and may also include agents that facilitate controlled release and other functionality related to biological release, biocompatibility, non-toxicity, microbial kill rate, manufacturability, shelf-life stability, and an optimized zone of inhibition (see below). The slow release binders and/or mediator compounds facilitate controlled emission of antimicrobial agent to the skin over a desired seven to ten day period. The adhesive of the adhesive portion 134 on the bottom side 128 of the antimicrobial member as well as the film layer 112 also may include at least one of an antimicrobial agent, an antifungal agent, and an antiseptic agent. The agents in the antimicrobial member, the adhesive, and the film layer may be the same or different.

In the embodiment shown in FIGS. 1 and 2, the antimicrobial member portions 130 may be generally parallel and spacedly disposed in proximity to each other, and the antimicrobial member portions may be disconnected in a railroad track type arrangement. In other words, the antimicrobial member 124 may include two separate, distinct portions that are generally parallel and close to each other to define the slot 132.

The slot 132, or at least a portion of the slot, may generally have a width (i.e., the distance between the two portions 130) approximately in the range of 0.05 inches to 0.4 inches. A zone of inhibition 137 defined by the antimicrobial member 124 covers an entire area of the slot 132 between the member portions 130. The zone of inhibition 137 is an area (such as a surface area of a patient's skin or catheter) around and extending beyond the physical boundaries of the antimicrobial member 124 in which colonization by certain microorganisms is inhibited. The zone of inhibition is dependent upon the type of microorganism. Thus, the zone of inhibition is larger for some microorganisms and smaller for others. In other words, certain microorganisms may survive closer to the antimicrobial member 124 than other microorganisms. Further, the effective zone of inhibition is different for every antimicrobial agent.

Figure 3:
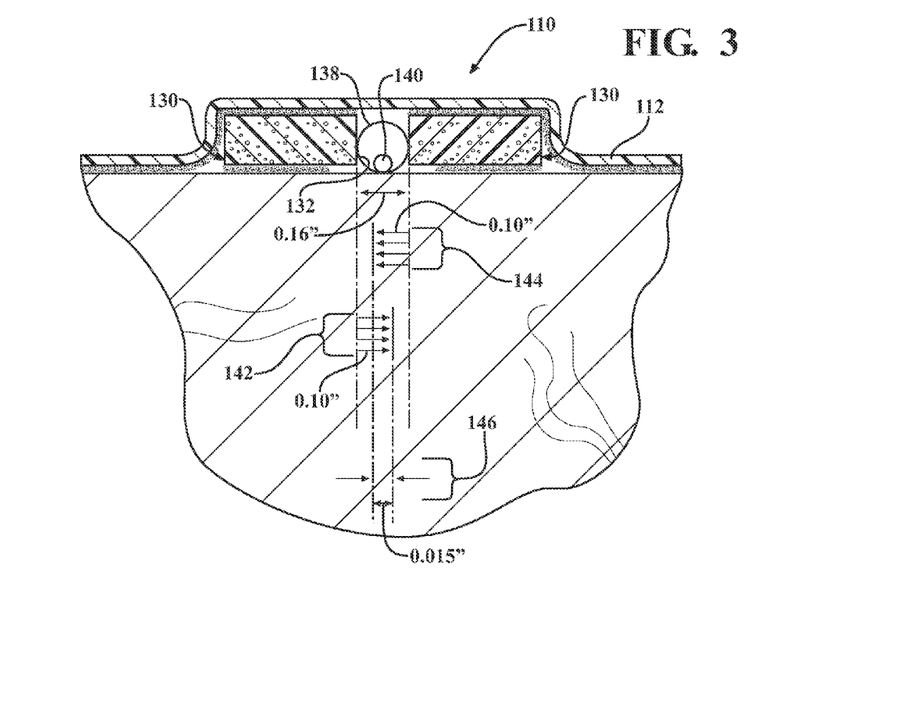
FIG. 3 is a schematic view illustrating a zone of inhibition of an antimicrobial member of the dressing.

For example, as shown schematically in FIG. 3 the width of the slot 132 may be approximately 0.184 inches. Since the zone of inhibition of each feature (portions, etc.) of the antimicrobial member 124 (for example loaded for antimicrobial CHG and more than a half dozen harmful microorganisms) generally extends 0.1 to 0.3 inches (3 mm to 7.7 mm) from the edges of the member depending on the targeted microorganisms, the entire area of the slot between the portions is within the zone of inhibition of the antimicrobial member. The elongation of the slot also maintains the zone of inhibition while allowing other dressing features (such as an integrated anchor, see below) to be aligned at their ideal locations (such as an anchor collar located near the back end of the bifurcation hub, or pigtails over a dressing notch, etc.), or the insertion site being close to an obstruction such as an EKG pad and the dressing needs to be moved away (such as by positioning the insertion site in the slot 132 at the far end of the dressing window).

More specifically, the largest typical vascular access catheter lumen outer diameters are found on introducer sheaths and is 14 FR (French scale), which is 0.184 inches (4.7 mm). The 14 FR catheter is shown schematically as reference numeral 138. The smallest typical vascular access catheter outer diameters are found on pediatric PICCs (peripherally inserted central venous catheters) and can be as small as 1 FR (approximately 0.013 inches) but are more typically 3 FR, which is 0.039 inches (1 mm). The 3 FR catheter is shown schematically as reference numeral 140. Therefore, the antimicrobial member portions 130 should be arranged such that the zone of inhibition reach of the antimicrobial agent (contained in the antimicrobial member) for the least penetrable microorganism extends from the inside wall of each portion 130 to a location within the area of the slot 132 that would fully be underneath the smallest (e.g., 0.04 inches in diameter) catheter lumen when the catheter is placed within the slot 132. And the portions 130 should be arranged such that the slot has a width that can accept that largest catheter lumen (e.g., 0.184 inches in diameter). As shown schematically, the zone of inhibition reach 142 of the left portion 130 into the slot 132 for the least CHG penetrable microorganism may be approximately 0.10, and similarly the zone of inhibition reach 144 of the right portion 130 into the slot 132 may be approximately 0.10. Therefore, the zone of inhibition reaches of the left and right portions 130 overlap a width of 0.015 inches (shown as reference numeral 146) generally down the center of the slot such that the overlap portion is completely under both the 3 FR catheter and the 14 FR catheter. Further, in use the antimicrobial member of the dressing may be disposed across or in femoral, jugular, antecubital fossa creases, fat folds, and the like. Thus, the width of the slot 132 may be made narrower so that when both a patient body crease and a narrower diameter (lower FR) catheter is present, there is still adequate zone of inhibition reach completely under and around the catheter. It is also possible that the antimicrobial member portions 130 may be arranged to accept a narrower range of catheter lumen sizes. For example, the width of the slot 130 can be set at a value that can accommodate 2 FR to 8.5 FR sized catheters within the zone of inhibition, or the width of the slot 130 can be set at a value that can accommodate 8.5 FR to 14.5 FR sized catheters within the zone of inhibition. The specific antimicrobial member, and thus the specific integrated overall dressing, chosen for use would then depend upon the size of the catheter used.

Figure 3A:
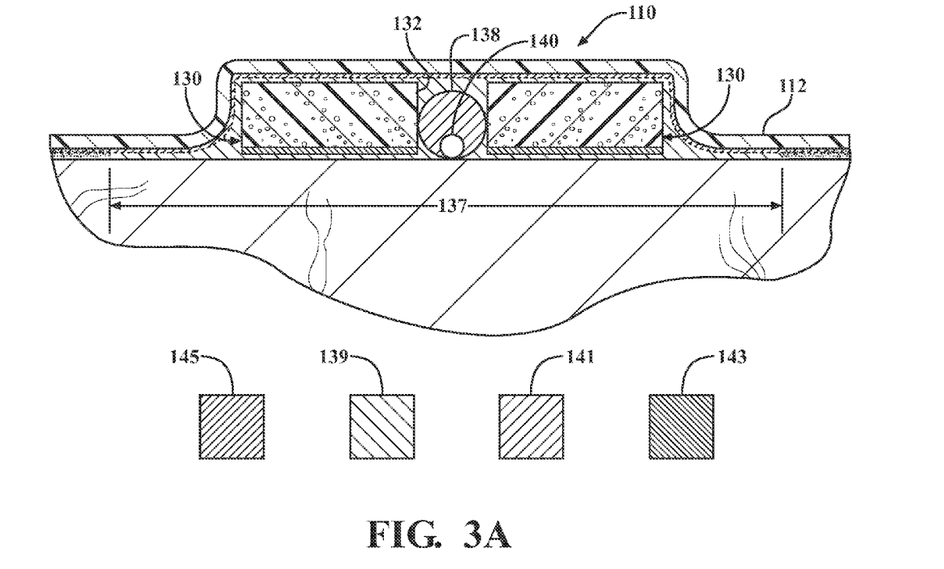
FIG. 3A is a schematic view similar to FIG. 3 illustrating zones of inhibition of the dressing.

Further, as shown schematically in FIG. 3A, the general entire left to right zone of inhibition reach of the antimicrobial member portions 130 is shown by zone of inhibition line 137. The zone of inhibition of the dressing 110 when covering a 14 FR catheter is shown by shading 139. The additional zone of inhibition of the dressing 110 when covering a smaller 2 FR catheter is shown by shading 141. The additional zone of inhibition contributed by the adhesive on the bottom of the antimicrobial member portions 130 if the adhesive includes an antimicrobial agent or similar is shown by shading 143. Similarly, the additional zone of inhibition contributed by the film layer 112 if the adhesive on the bottom of the film layer includes an antimicrobial agent or similar is shown by shading 145.

In use, the dressing 110 is disposed over a catheter insertion site such that the insertion site and catheter lumen extending from the insertion site are disposed within the slot 132 of the antimicrobial member 124. Thus, the insertion site and catheter lumen surrounded by the antimicrobial member 124 are entirely within the member's zone of inhibition, and the antimicrobial member forms a barrier against colonization and infection of the insertion site. Microorganisms may be found on a patient's skin, the subcutaneous catheter insertion tract, or in the patient's blood and/or may be introduced via the catheter or a medical clinician's hands. Microorganism colonization at or around a patient catheter insertion site can undesirably lead to catheter related blood stream infection ("CRBSI"), a serious prognosis that typically costs in the range of $10,000 to $40,000 to treat and potentially can lead to death.

The antimicrobial member 124 may have a low profile, i.e. a low height of, for example, approximately 1/16 of an inch. However, the antimicrobial member is not limited to a specific profile, and may have a height of closer to 1/4 of an inch as shown in the embodiments below.

Figure 4:
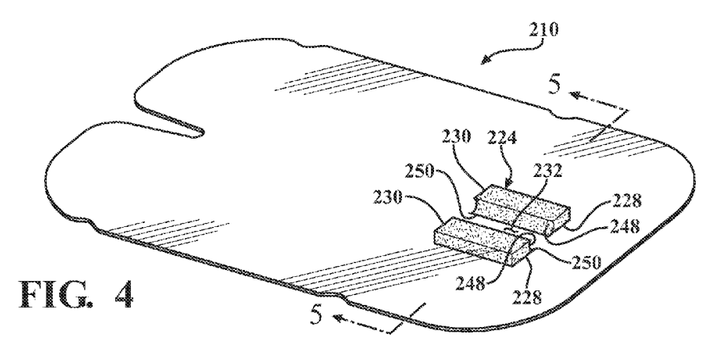
FIG. 4 is a perspective view of an alternative embodiment of a dressing having integral antimicrobial in accordance with the invention.
Figure 5:
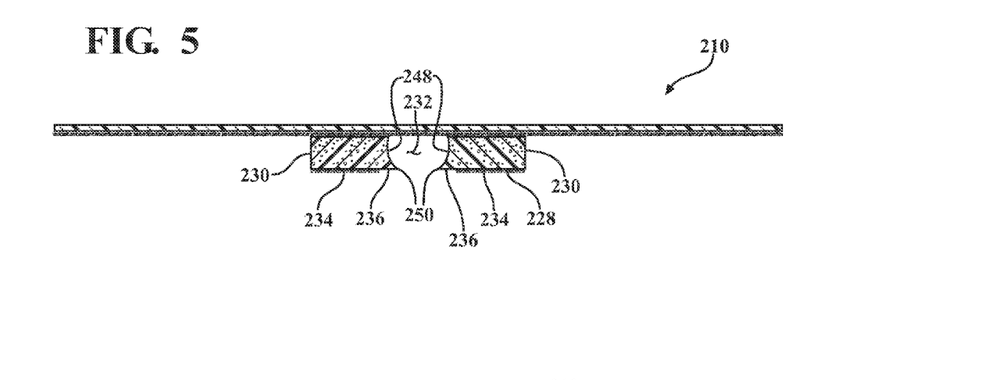
FIG. 5 is a cross-sectional view taken along the line 5-5 in FIG. 4.

In another embodiment 210 shown in FIGS. 4 and 5, each portion 230 of the antimicrobial member 224 may include a curved sidewall 248 adjacent to and facing the slot 232. For instance, the sidewall may have a semi-circular cross-section. The curved sidewalls 248 aide in retaining a catheter lumen (and medical tubing in general) in the slot 232. Each portion 230 also may include a blade 250 extending along the bottom side 228 from the curved sidewall 248 towards the other of the portions, i.e. inwardly into the slot 232. The blades 250 effectively reduce the width of the slot close to a patient's skin, allowing the gap (width) between the portions 230 to be smaller adjacent the patient's skin, which is important for maintaining a sufficient zone of inhibition for smaller OD catheters such as 2-3 FR catheters. The antimicrobial member bottom side may include both an adhesive portion 234 and an adhesive free portion 236 adjacent the slot that generally corresponds with the blades 250, i.e., the blades do not have any adhesive thereon. This configuration also helps to keep the lumen from pressing too far into a patient's skin, which can reduce the antimicrobial's crawl distance in the compressed area between the top of the skin and the catheter bottom.

Figure 6:
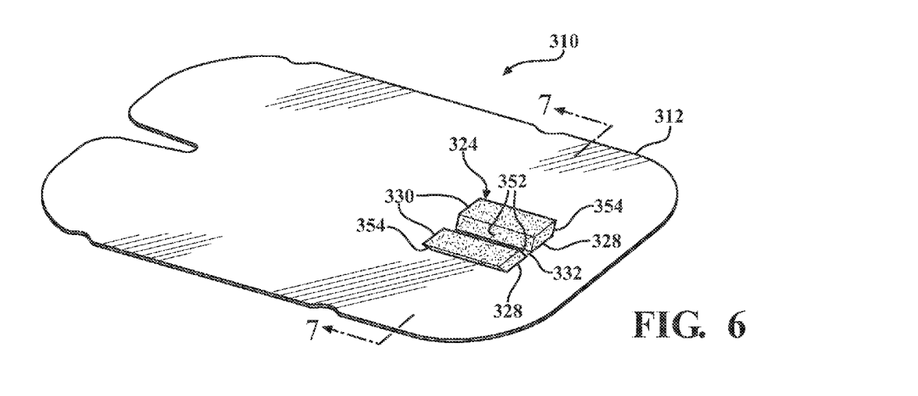
FIG. 6 is a perspective view of an alternative embodiment of a dressing having integral antimicrobial in accordance with the invention.
Figure 7:
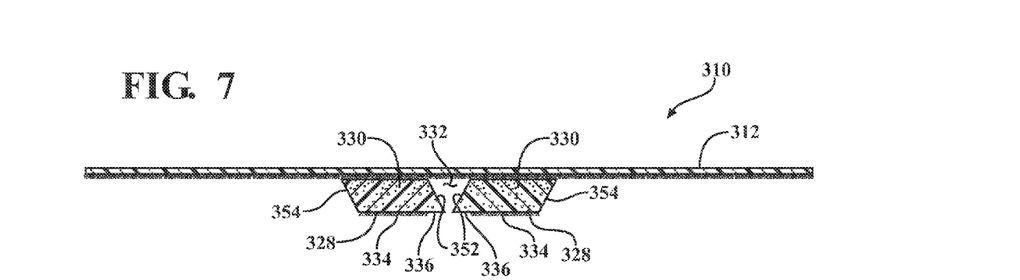
FIG. 7 is a cross-sectional view taken along the line 7-7 in FIG. 6.

In another embodiment 310 shown in FIGS. 6 and 7, each portion 330 of the antimicrobial member 324 may include a sloped inner sidewall 352 such that the slot 332 is tapered towards the antimicrobial member bottom side 328. Each portion 330 may also include a sloped outer sidewall 354 that is tapered inwardly towards the slot 332 in a direction from the film layer 312 to the bottom side 328 of the portion 330. The sloped sidewalls 352, 354 reduce tenting of the film layer 312 over a patient's skin when the dressing is applied to a patient's skin. In other words, the sloped sidewalls 352, 354 reduce the amount of open space between the patient's skin and the dressing and/or the height of the dressing over the patient's skin. The sloped sidewalls 352, 354 also cause the film layer to pivot the portions 330 such that the width of the slot is reduced, i.e., the gap distance between the portions 330 is reduced when the dressing is applied to patient's skin, and the slot 332 can be pivoted open by bending the dressing prior to applying it to patient's skin. The antimicrobial member bottom side 328 may include both an adhesive portion 334 and an adhesive free portion 336 adjacent the slot. This configuration also helps to keep the catheter from pressing too hard against the skin, which reduces suppression of the zone of inhibition caused by "mash down" lockout.

Figure 8:
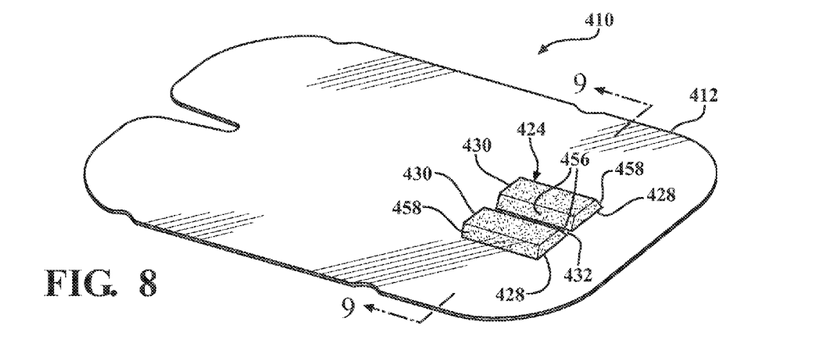
FIG. 8 is a perspective view of an alternative embodiment of a dressing having integral antimicrobial in accordance with the invention.
Figure 9:
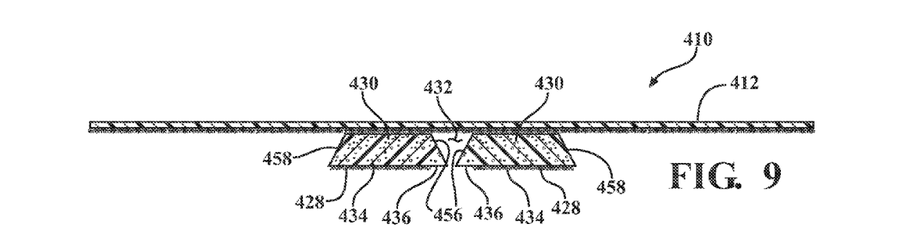
FIG. 9 is a cross-sectional view taken along the line 9-9 in FIG. 8.

In another embodiment 410 shown in FIGS. 8 and 9, each portion 430 of the antimicrobial member 424 may include a sloped inner sidewall 456 such that the slot 432 is tapered towards the antimicrobial member bottom side 428. Each portion 430 may also include a sloped outer sidewall 458 that is tapered outwardly away from the slot 432 in a direction from the film layer 412 to the bottom side 428 of the portion 430. Each portion 430 thus has a truncated triangular cross-sectional shape. As in the embodiment above, the sloped sidewalls 456, 458 reduce tenting of the film layer 412 and allow the slot to be pivoted open and closed. The antimicrobial member bottom side 428 may include both an adhesive portion 434 and an adhesive free portion 436 adjacent the slot.

Figure 10:
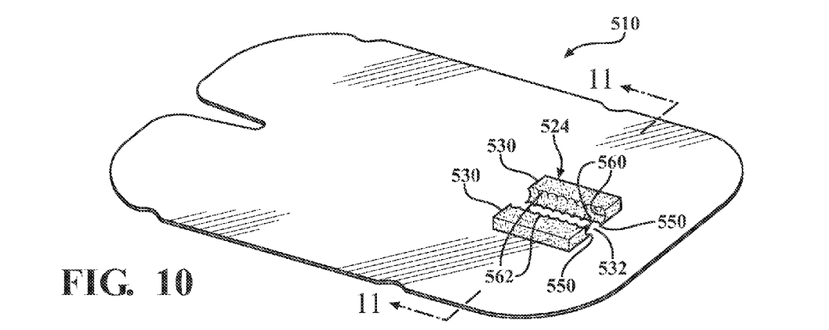
FIG. 10 is a perspective view of an alternative embodiment of a dressing having integral antimicrobial in accordance with the invention.
Figure 11:
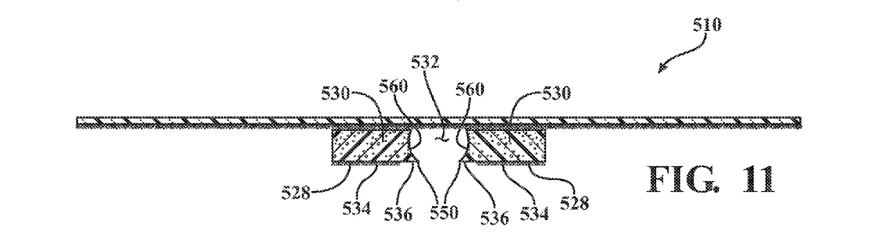
FIG. 11 is a cross-sectional view taken along the line 11-11 in FIG. 10.

In another embodiment 510 shown in FIGS. 10 and 11, each portion 530 of the antimicrobial member 524 may include a sidewall 560 adjacent to and facing the slot 532 that has a scalloped surface including scallops 562 vertically disposed along the length of the slot 532. The scallops 562 aide in snugly securing in a conforming fashion, a catheter or other medical tubing in the slot 532 around the vertical portion as it emanates from the insertion site after being bent over ninety degrees parallel to the skin. Each portion 530 also may include a blade 550 extending along the bottom side 528 from the scalloped sidewall 560 towards the other of the portions, i.e. inwardly into the slot 532. Any scallop encircles the vertical portion of lumen, allowing the blade to nestle up tightly under the horizontal portion of lumen. The antimicrobial member bottom side 528 may include both an adhesive portion 534 and an adhesive free portion 536 adjacent the slot 532 that generally corresponds with the blades 564, i.e., the blades do not have any adhesive thereon, to facilitate closure around the vertical and horizontal portions of the catheter emanating from the insertion site, to reach as far under the catheter as possible.

Figure 12:
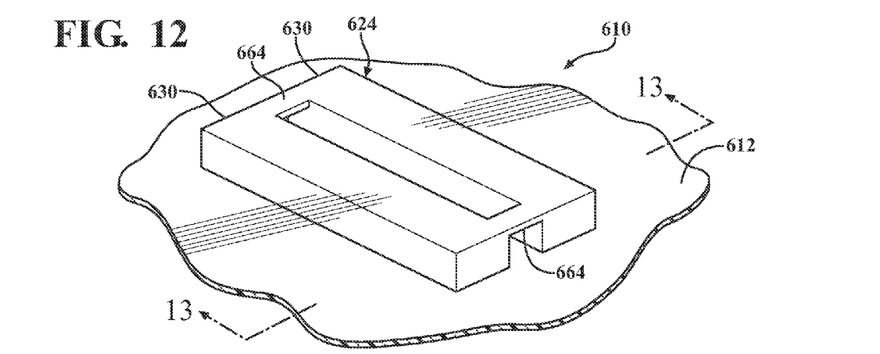
FIG. 12 is a perspective view of an alternative embodiment of a dressing having integral antimicrobial in accordance with the invention.
Figure 13:
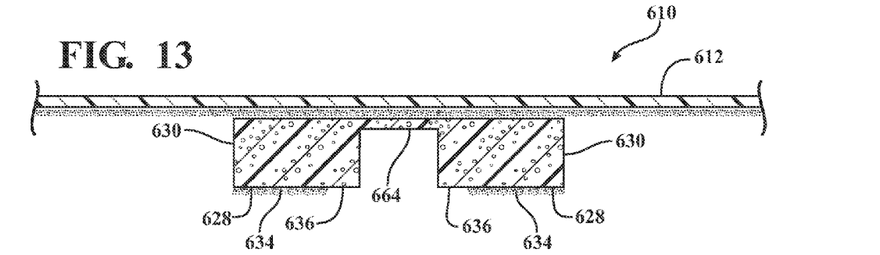
FIG. 13 is a cross-sectional view taken along the line 13-13 in FIG. 12.

In another embodiment 610 shown in FIGS. 12 and 13, the antimicrobial member 624 may include at least one crossover tie 664 connecting the portions 630. In the embodiment 610, the antimicrobial member 624 includes a tie 664 at each end of the portions 630. The ties 664 may each have a height that is less than the height of the portions 630, and the ties 664 may be disposed generally adjacent and/or may be adhered to the film layer 612. The ties 664 stabilize the antimicrobial member 624 and aide in manufacturing and in maintaining a generally parallel disposition between the portions 630. The ties 664 also prevent against a catheter or other medical tubing pushing the antimicrobial member 624 and/or the film layer 612 up and away from a patient's skin in an area in which the antimicrobial member crosses or lies over the catheter. When more than one tie 664 is present, the ties 664 may have different thicknesses, as one end of the antimicrobial member is usually not crossing over the catheter lumen, or alternatively they may have generally the same thickness as shown.

The ties 664 allow the antimicrobial member to cross over the catheter without pushing the antimicrobial member up and away from a patient's skin. This is important when the conditions are such that, when the dressing is applied to a patient, the cross-over ties land on or near to a location within about one-half to three-quarters of an inch from the insertion site, which may occur, for example, when the catheter French OD size is generally large (i.e., 7 FR and up). In such a case, the bottom side 628 of the antimicrobial member 624 (and the rest of the dressing layer(s), e.g. the film layer) may become tented away from the skin at and around the insertion site, decreasing the reach of the zone of inhibition of the antimicrobial member to a level that may less than effectively inhibit colonization at the main target, which is an area of approximately one-half to one inch in radius around the insertion site. However, the cross-over ties 664 define a channel between the dressing and a patient's skin through which the catheter lumen can pass without pushing the dressing away from the patient's skin, and the zone of inhibition of the antimicrobial member is preserved. The antimicrobial member bottom side 628 may also include both an adhesive portion 634 and an adhesive free portion 636 adjacent the slot 632.

Figure 14:
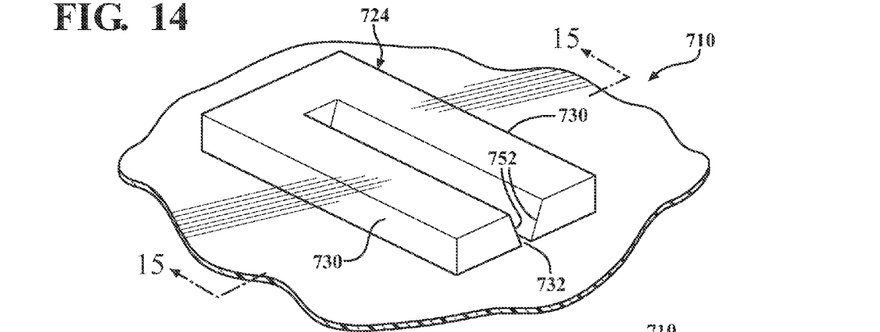
FIG. 14 is a perspective view of an alternative embodiment of a dressing having integral antimicrobial in accordance with the invention.
Figure 15:
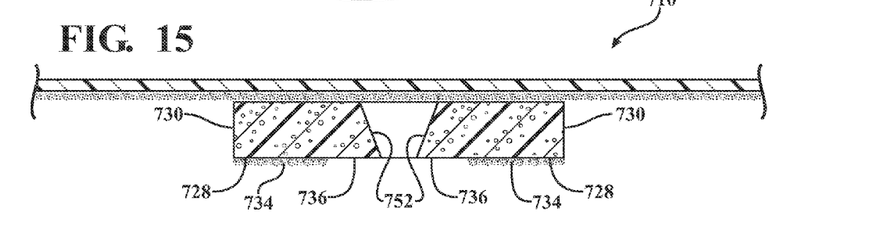
FIG. 15 is a cross-sectional view taken along the line 15-15 in FIG. 14.

In another embodiment 710 shown in FIGS. 14 and 15, the antimicrobial member 724 may be bifurcated such that the portions 730 define prongs of the bifurcated, fork-like shaped antimicrobial member. Each portion 730 of the antimicrobial member 724 may include a sloped inner sidewall 752 such that the slot 732 is tapered towards the antimicrobial member bottom side 728. The antimicrobial member bottom side 728 may also include both an adhesive portion 734 and an adhesive free portion 736 adjacent the slot 732.

Figure 16:
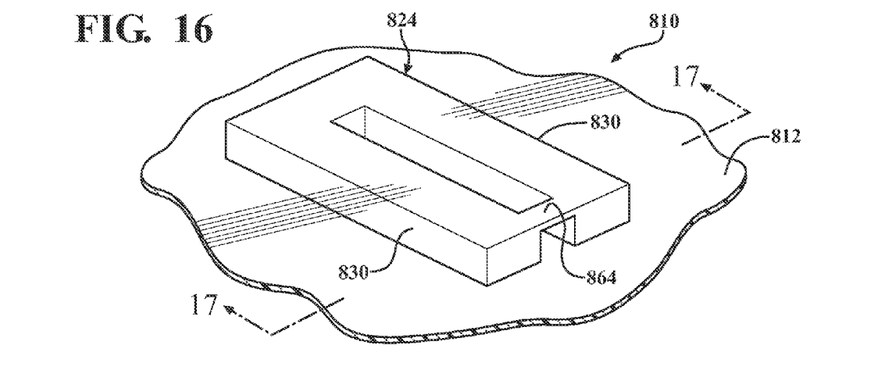
FIG. 16 is a perspective view of an alternative embodiment of a dressing having integral antimicrobial in accordance with the invention.
Figure 17:
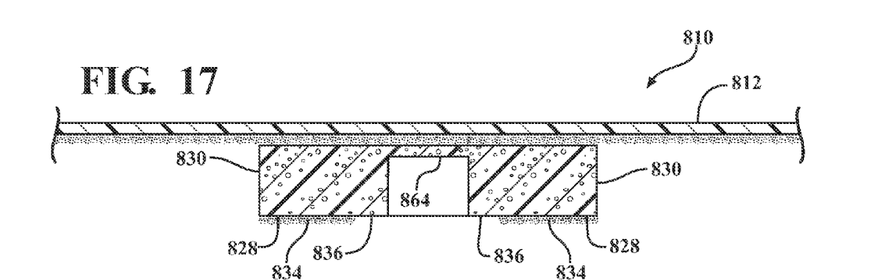
FIG. 17 is a cross-sectional view taken along the line 17-17 in FIG. 16.

In another embodiment 810 shown in FIGS. 16 and 17, the bifurcated antimicrobial member may include a cross-over tie 864 connecting the prong portions 830, and as described above, the tie may have a height that is less than the height of the portions, and the tie 864 may be disposed generally adjacent and/or may be adhered to the film layer 812. The tie 864 stabilizes the antimicrobial member 824 and aides in maintaining a generally parallel disposition between the portions 830. The ties 864 also prevent against a catheter or other medical tubing pushing the antimicrobial member 824 and/or the film layer 812 up and away from a patient's skin in an area in which the antimicrobial member crosses or lies over the catheter. The cross-over tie 864 defines a channel between the dressing and a patient's skin through which the catheter lumen can pass without pushing the dressing away from the patient's skin, and the zone of inhibition of the antimicrobial member is preserved. The antimicrobial member bottom side 828 may also include both an adhesive portion 834 and an adhesive free portion 836 adjacent the slot 832.

Although not shown, the antimicrobial member alternatively may have three prongs and thus two insertion site/catheter lumen accepting slots. In another alternative, the antimicrobial member may have four prongs and thus three insertion site/catheter lumen accepting slots. Further, in yet another embodiment, the antimicrobial member may have a bifurcated, fork-like shape wherein the distance between the two prongs includes a narrow portion and an increased width portion. The narrow portion is for placement adjacent to either side of the insertion site and catheter lumen extending therefrom, and the bifurcation may have a gap width between the prongs approximately within the range of 0.05 to 0.4 inches in the narrow portion. The increased width portion is for placement further away from the insertion site towards the catheter hub and has a gap width between the prongs that increases toward distal ends of the prongs. The increased width between the prongs at the distal ends of the prongs may allow for off-axis placement of the dressing yet having the insertion site within the zone of inhibition, or the placement of a catheter hub or similar within the boundaries of the antimicrobial member, which aides a clinician in placing the integrated dressing over an insertion site, lumen, and catheter hub.

Figure 18:
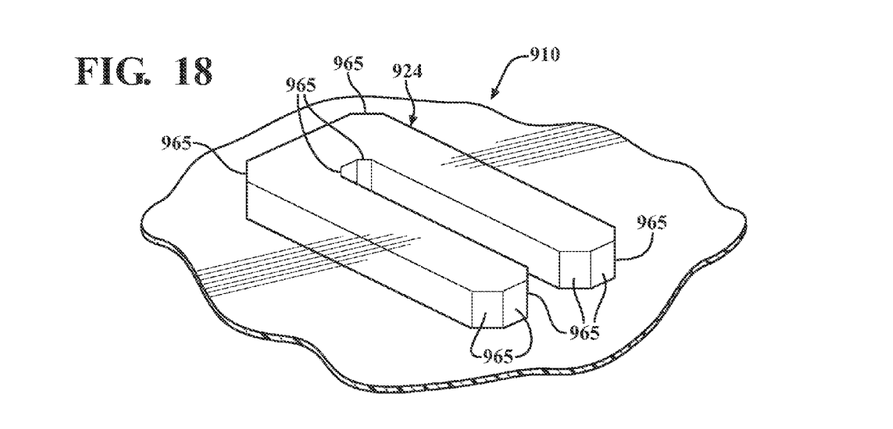
FIG. 18 is a perspective view of an alternative embodiment of a dressing having integral antimicrobial in accordance with the invention.

In another embodiment 910 shown in FIG. 18, the antimicrobial member 924 may have rounded or cut-off edges 965.

Figure 19:
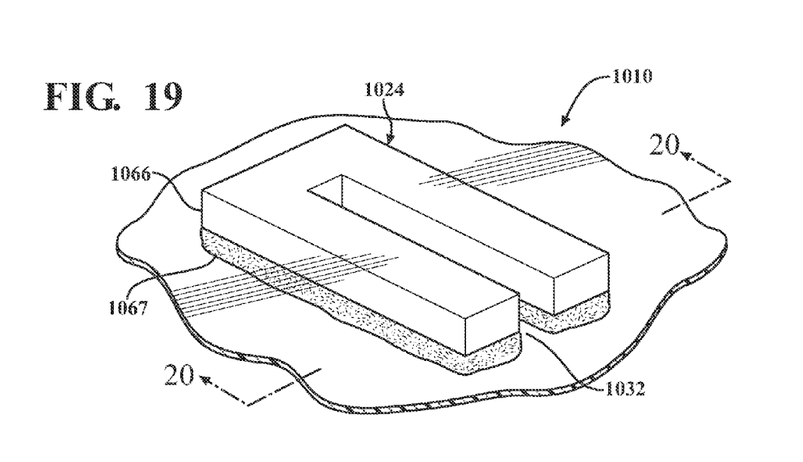
FIG. 19 is a perspective view of an alternative embodiment of a dressing having integral antimicrobial in accordance with the invention.
Figure 20:
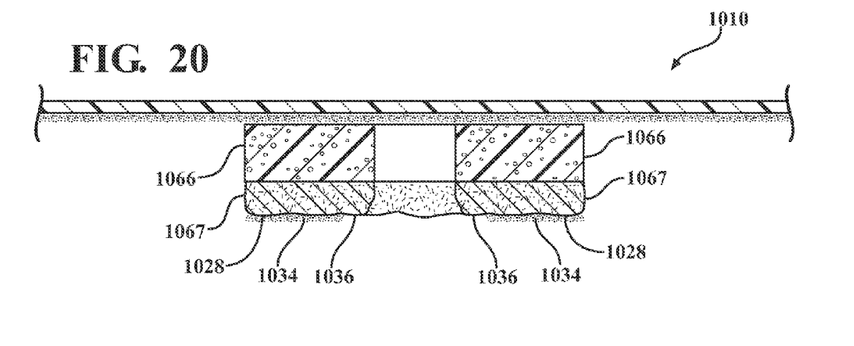
FIG. 20 is a cross-sectional view taken along the line 20-20 in FIG. 19.

In another embodiment 1010 shown in FIGS. 19 and 20, the antimicrobial member 1024 may be a dual-density member including a foam layer 1066 and an adjacent cotton layer 1067 disposed underneath the foam layer and defining the bottom side 1028 of the antimicrobial member. The antimicrobial member bottom side 1028 may also include both an adhesive portion 1034 and an adhesive free portion 1036 adjacent the slot 1032.

The antimicrobial member may also include a stability foot at an end of each of the member portions that extends outwardly and generally orthogonal to the slot. In this embodiment, each member portion may therefore have a generally L-shaped end. The stability feet provide each member portion of the dressing with an integrally connected lever feature, which when pressed in the center thereof from the top of the dressing with the thumb of one hand, while spreading the second and third fingers of the same hand holding the underside of the dressing release liner (not shown in the drawings) cause the inner side walls at the bottom of the antimicrobial member portions to move apart (opening the slot) allowing smooth placement of the dressing over catheter lumen as the dressing is being applied to a patient's skin.

It should be understood that an antimicrobial member in accordance with the present invention may have any combination of the structures and features described above.

The dressing having the integral antimicrobial allows for transparent viewing, including over and through the slot, of the insertion site through the clear transparent film layer during the dressing installation and during the dressing dwell time on a patient's skin. The transparent view of the insertion site allows clinicians to check for blood, exudate, redness, swelling, eschar, and other patient wound issues at the insertion site while the dressing is in place. In contrast, conventional antimicrobial, separate piece dressings/devices distort, tint, color, or totally block the view of the insertion site.

Figure 21:
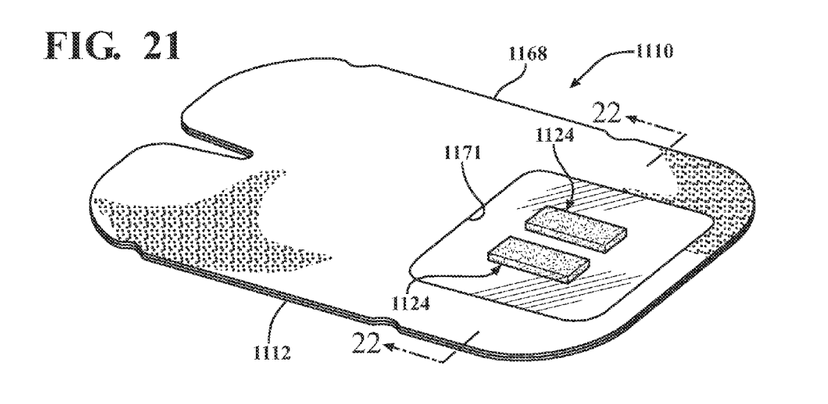
FIG. 21 is a perspective view of an alternative embodiment of a dressing having integral antimicrobial in accordance with the invention.
Figure 22:
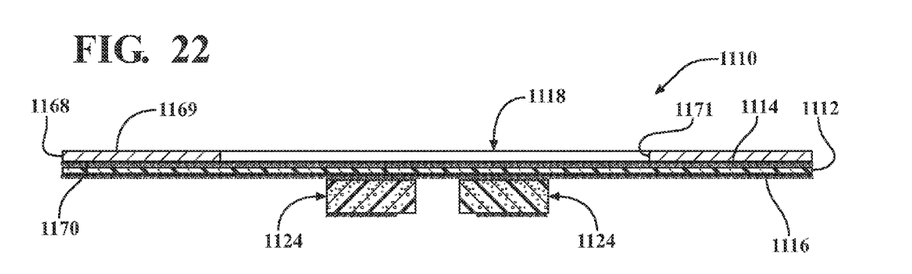
FIG. 22 is a cross-sectional view taken along the line 22-22 in FIG. 21.

Turning to FIGS. 21 and 22, an integrated antimicrobial dressing 1110 in accordance with the present invention may further include a fabric layer 1168 having a top side 1169, an opposite bottom side 1170, and an opening 1171 therein defining the insertion site viewing portion 1118. The fabric layer may be adhered to one of the film layer 1112 top side 1114 or the film layer bottom side 1116. The film layer 1112 generally closes the opening 1171 in the fabric layer 1168, and the film layer is adhered around the opening such that the film layer extends beyond the edge of the opening. The fabric layer 1168 may be any suitable woven or non-woven fabric material. The dressing 1110 includes an antimicrobial member 1124 having any combination of the features described above.

Figure 23:
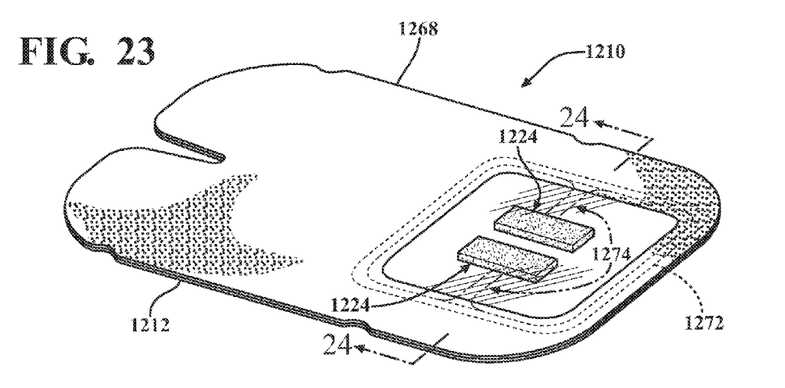
FIG. 23 is a perspective view of an alternative embodiment of a dressing having integral antimicrobial in accordance with the invention.
Figure 24:
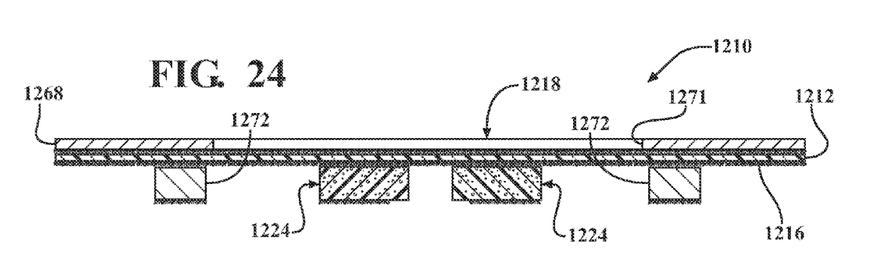
FIG. 24 is a cross-sectional view taken along the line 24-24 in FIG. 23.

Optionally, as shown in FIGS. 23 and 24 the dressing 1210 may also include an absorbent pad 1272 adhered to the film layer 1212 bottom side 1216. The absorbent pad 1272 may be generally disposed in or adjacent to the insertion site viewing portion 1218. For example, the absorbent pad 1272 may generally circumscribe the insertion site viewing portion and/or the absorbent pad may generally lie along the perimeter of the opening 1271 in the fabric layer 1268, if present. The absorbent pad 1272 also may be generally disposed outside of the antimicrobial member 1224 such that the absorbent pad partially or entirely surrounds the antimicrobial member. The absorbent pad 1272 absorbs excess fluids, exudate, etc. that is not absorbed by the antimicrobial member 1224. The antimicrobial member 1224 may have any combination of the features described above. Further, a link member 1274 (shown in phantom line in FIG. 23) that is made of an absorbent material or similar may form an isthmus that connects the absorbent pad 1272 to the antimicrobial member 1224. For example, the dressing may include two link members 1274, and each link member may connect the absorbent pad 1272 to one of the antimicrobial member portions. The link member(s) 1274 increase the absorbent capacity of the dressing and provide for wicking of fluid, exudates, etc. from the absorbent pad 1272 toward the antimicrobial member 1224.

Figure 25:
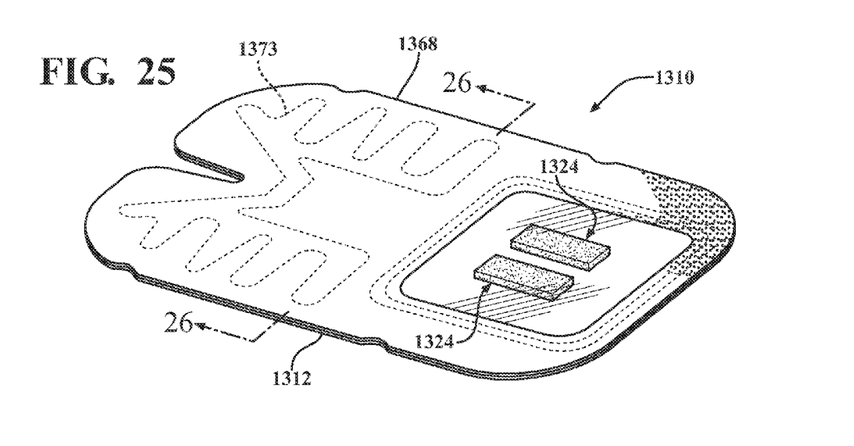
FIG. 25 is a perspective view of an alternative embodiment of a dressing having integral antimicrobial in accordance with the invention.
Figure 26:
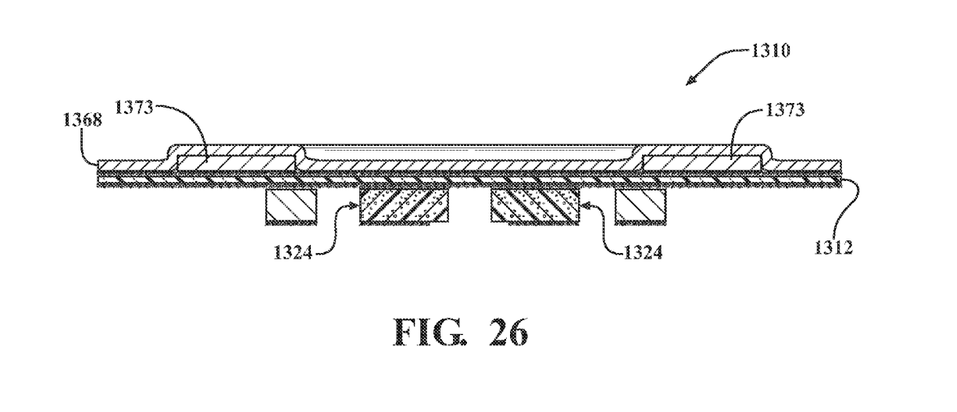
FIG. 26 is a cross-sectional view taken along the line 26-26 in FIG. 25.
Figure 27:
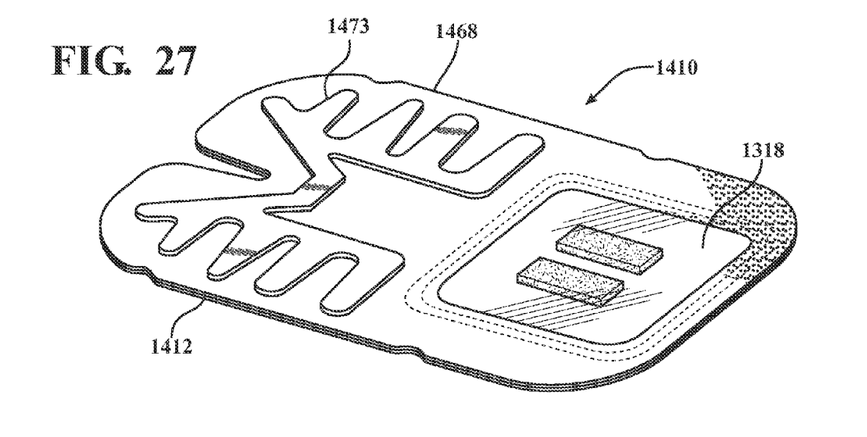
FIG. 27 is a perspective view of an alternative embodiment of a dressing having integral antimicrobial in accordance with the invention.

In another embodiment shown in FIGS. 25 and 26, an integrated antimicrobial dressing 1310 in accordance with the present invention may further include an integral anchor member 1373 including a reinforcing structure that strengthens the dressing and resists tugging and pull forces from peeling the dressing away from a patient's skin once the dressing has been applied. The anchor member 1373 is adhered to one of the fabric layer top side or the fabric layer bottom side. For example, the anchor member 1373 may be disposed between the fabric layer 1368 and the film layer 1312. Alternatively, as shown in FIG. 27, in an embodiment 1410 the anchor member 1473 may be disposed on top of the fabric layer 1468 which is on top of film layer 1412. The anchor member is also typically disposed outside of the insertion site viewing portion 1318. The dressing 1310 includes an antimicrobial member 1324 having any combination of the features described above.

It should be understood that an integrated antimicrobial dressing in accordance with the present invention may have any combination of the stack layers described above.

Figure 28:
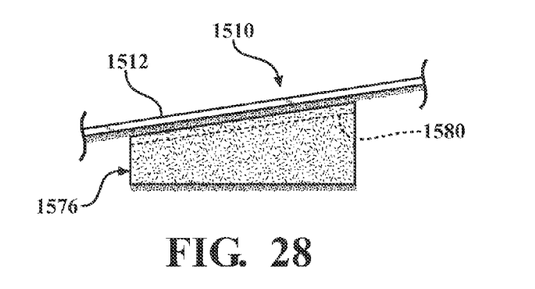
FIG. 28 is a side view of an alternative embodiment of a dressing having integral antimicrobial in accordance with the invention.
Figure 29:
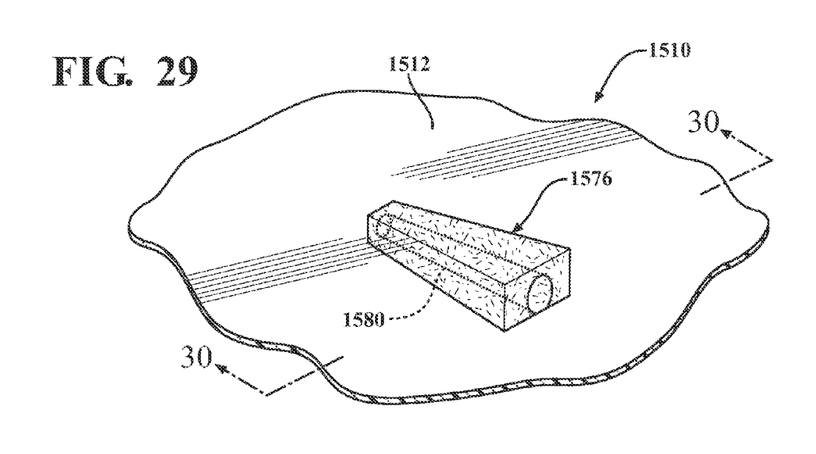
FIG. 29 is a perspective view of the dressing of FIG. 28.
Figure 30:
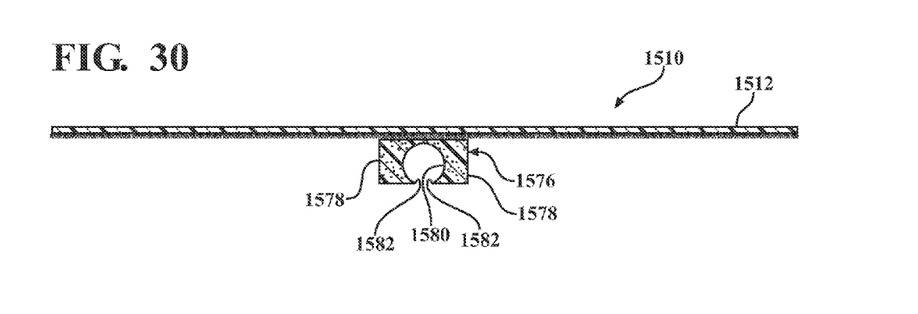
FIG. 30 is a cross-sectional view taken along the line 30-30 in FIG. 29.

In yet another alternative embodiment shown in FIGS. 28 through 30, an integrated antimicrobial dressing 1510 in accordance with the present invention may include a film layer 1512 and a tapered antimicrobial member 1576. The antimicrobial member 1576 is tapered both in height from one longitudinal end of the member to the opposite end as well as in width between these same ends. Elongated portions 1578 of the antimicrobial member 1576 define a slot 1580 therebetween. The slot 1580 may also have a tapered size that increases from one end of the member 1576 to the opposite end. For example, the "large" end of the slot 1580 may be 1.5 to 3 times the size of the "small" end of the slot. The taper of the member 1576 and/or the slot 1580 aides in fitting the member over, around, and under catheter introducer sheaths having increasing diameter sheath bifurcation hub noses. The elongated portions 1578 may also each include a blade 1582 (similar to the blades 250 described above) that slides under the catheter and/or hub when the dressing is applied to a patient.

Figure 31:
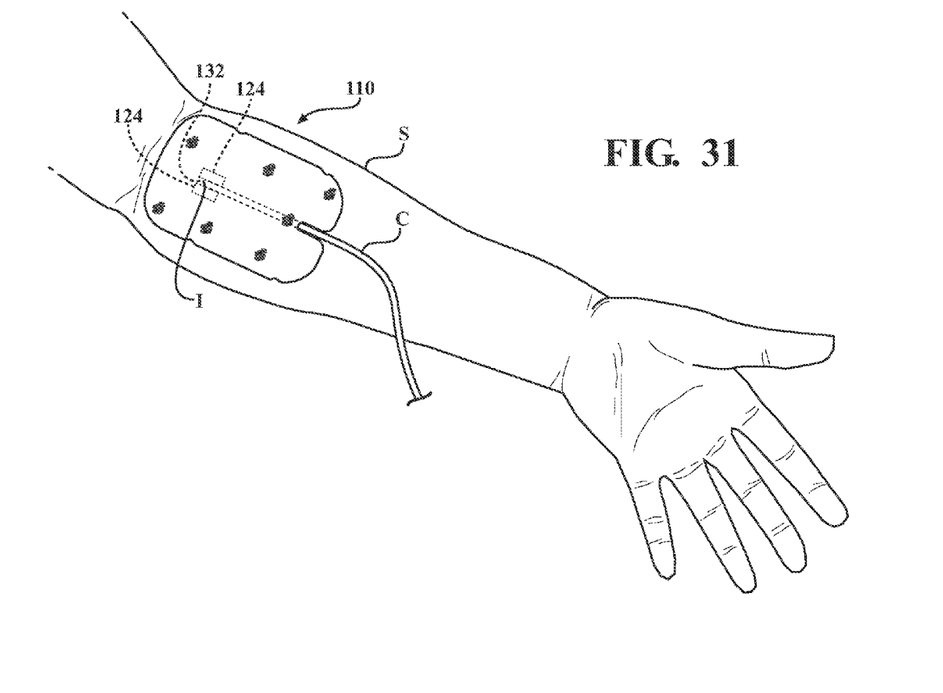
FIG. 31 is an environmental view of the dressing having integral antimicrobial applied to a patient's skin.

Turning to FIG. 31, the dressing 110 may be applied to a patient's skin S around a catheter insertion site I. The dressing 110 specifically may be positioned in a manner such that the insertion site I lies in the slot 132 between the antimicrobial member portions. The catheter C extending from the catheter insertion site I also lies in and extends out of the slot 132 such that the catheter insertion site I and catheter C are within the zone of inhibition of the antimicrobial member 124. Thus, the antimicrobial member 124 forms a barrier against colonization and infection of the insertion site I.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A dressing comprising:
   a transparent film layer having a top side, an opposite bottom side, and an insertion site viewing portion; and
   a fabric layer having a top side, an opposite bottom side, and an opening therein;
   said fabric layer being adhered to one of said film layer top side and said film layer bottom side and said opening defining said insertion site viewing portion;
   an antimicrobial member having a top side and an opposite bottom side, said antimicrobial member top side being adhered to said transparent film layer bottom side in said insertion site viewing portion;
   said antimicrobial member including at least one pair of elongated, spacedly disposed portions defining a slot therebetween, the slot having a width sized to accept a catheter lumen;
   wherein a zone of inhibition defined by said antimicrobial member entirely covers the slot.

2. The dressing of claim 1, wherein said antimicrobial member bottom side includes an adhesive thereon.

3. The dressing of claim 2, wherein said antimicrobial member bottom side includes an adhesive free portion adjacent said slot.

4. The dressing of claim 2, wherein said adhesive includes at least one of an antimicrobial agent, an antifungal agent, an antiseptic agent, an antibacteriocidal agent, and an antiviral agent.

5. The dressing of claim 1, including an absorbent pad adhered to said transparent film layer bottom side.

6. The dressing of claim 5, wherein said absorbent pad is generally disposed in or adjacent to said insertion site viewing portion.

7. The dressing of claim 5, wherein said absorbent pad is generally disposed outside of said antimicrobial member.

8. The dressing of claim 5, including an absorbent pad link member that connects said absorbent pad to said antimicrobial member.

9. The dressing of claim 1, wherein each said spacedly disposed portion includes a curved sidewall adjacent said slot.

10. The dressing of claim 9, wherein each said spacedly disposed portion includes a blade extending from said curved sidewall towards the other of said spacedly disposed portions.

11. The dressing of claim 1, including an anchor member including a reinforcing structure, said anchor member being adhered to one of said fabric layer top side and said fabric layer bottom side.

12. The dressing claim 11, wherein said anchor member is disposed between said fabric layer and said film layer.

13. The dressing of claim 11, wherein said anchor member is disposed outside of said insertion site viewing portion.

14. The dressing of claim 1, wherein said transparent film layer bottom side includes an adhesive thereon.

15. The dressing of claim 1, wherein said transparent film layer bottom side includes an adhesive portion and an adhesive-free portion, said adhesive-free portion being disposed in said slot between said antimicrobial member portions.

16. The dressing of claim 1, wherein said antimicrobial member bottom side has no adhesive thereon.

17. The dressing of claim 1, wherein said slot has a width approximately in the range of 0.05 inches to 0.4 inches.

18. The dressing of claim 1, wherein said antimicrobial member includes at least one of an antimicrobial agent, an antifungal agent, an antiseptic agent, an antibacteriocidal agent, and an antiviral agent.

19. The dressing of claim 1, wherein said antimicrobial member is made of a carrier material impregnated with at least one of an antimicrobial agent, an antifungal agent, an antiseptic agent, an antibacteriocidal agent, and an antiviral agent, and including a slow release binder.

20. The dressing of claim 1, wherein said pair of spacedly disposed portions are generally parallel.

21. The dressing of claim 1, wherein said pair of spacedly disposed portions are disconnected.

22. The dressing of claim 1, wherein said antimicrobial member is bifurcated such that said spacedly disposed portions define prongs of the bifurcated antimicrobial member.

23. The dressing of claim 1, wherein said antimicrobial member includes at least one tie connecting said spacedly disposed portions, said tie having a height that is less than a height of said portions.

24. The dressing of claim 1, wherein each said pair of spacedly disposed portion includes a sloped sidewall such that said slot is tapered towards said antimicrobial member bottom side.

25. The dressing of claim 1, wherein each said spacedly disposed portion includes a sidewall adjacent said slot, said sidewall having a scalloped surface facing said slot.

26. The dressing of claim 1, wherein said antimicrobial member includes a carrier layer and an adjacent fibrous layer.

\* \* \* \* \*